United States Patent
Bedingham et al.

(10) Patent No.: US 9,204,856 B2
(45) Date of Patent: Dec. 8, 2015

(54) ELECTRONIC STETHOSCOPE SYSTEM FOR TELEMEDICINE APPLICATIONS

(75) Inventors: William Bedingham, Woodbury, MN (US); Craig D. Oster, Oakdale, MN (US); Daniel J. Rogers, Grant, MN (US)

(73) Assignee: 3M Innovative Properties Company, St. Paul, MN (US)

(*) Notice: Subject to any disclaimer, the term of this patent is extended or adjusted under 35 U.S.C. 154(b) by 1448 days.

(21) Appl. No.: 12/910,086

(22) Filed: Oct. 22, 2010

(65) Prior Publication Data

US 2011/0190665 A1    Aug. 4, 2011

Related U.S. Application Data

(60) Provisional application No. 61/300,285, filed on Feb. 1, 2010.

(51) Int. Cl.
*A61B 7/04* (2006.01)

(52) U.S. Cl.
CPC .................................... *A61B 7/04* (2013.01)

(58) Field of Classification Search
CPC ............ A61B 7/02; A61B 7/04; A61B 7/045; A61B 7/003; A61B 2562/0204
See application file for complete search history.

(56) References Cited

U.S. PATENT DOCUMENTS

| | | | |
|---|---|---|---|
| 5,492,129 A | 2/1996 | Greenberger | |
| 5,498,841 A | 3/1996 | Allen | |
| 5,561,275 A | 10/1996 | Savage | |
| 5,812,678 A | 9/1998 | Scalise et al. | |
| 5,825,895 A | 10/1998 | Grasfield et al. | |
| 5,841,846 A | 11/1998 | Abbruscato | |
| 6,134,331 A | 10/2000 | Baekgaard | |
| 6,340,350 B1 | 1/2002 | Sims | |
| 6,540,673 B2 | 4/2003 | Gopinathan et al. | |
| 6,544,198 B2 | 4/2003 | Chong et al. | |
| 7,006,638 B1 | 2/2006 | Baekgaard et al. | |
| 7,115,102 B2 | 10/2006 | Abbruscato | |
| 7,130,429 B1 | 10/2006 | Dalgaard et al. | |
| 7,444,285 B2 | 10/2008 | Forbes | |
| 2002/0085724 A1 | 7/2002 | Grasfield | |

(Continued)

FOREIGN PATENT DOCUMENTS

| | | |
|---|---|---|
| EP | 1943952 | 6/2008 |
| JP | 2001-333899 | 12/2001 |
| WO | WO 2008035211 | 3/2008 |

OTHER PUBLICATIONS

Search Report for PCT/US10/48745.

*Primary Examiner* — Max Hindenburg

(57) ABSTRACT

An electronic stethoscope includes a housing configured for hand-held manipulation, a transducer supported by the housing and configured to sense auscultation signals at a first location, and a headset coupled to the housing and configured to deliver audio corresponding to the auscultation signals through earpieces on the headset. The electronic stethoscope further includes a processor disposed in the housing and configured to convert the auscultation signals to first digital signals representative of the auscultation signals and to wirelessly transmit the first digital signals from the electronic stethoscope via a secure digital network to a second location such that the audio corresponding to the auscultation signals is provided to headsets of one or more additional electronic stethoscopes at the second location in substantial real time with the sensing of the auscultation sounds at the first location.

13 Claims, 8 Drawing Sheets

(56) References Cited

U.S. PATENT DOCUMENTS

| | | |
|---|---|---|
| 2003/0002685 A1 | 1/2003 | Werblud |
| 2004/0068194 A1 | 4/2004 | Johnson |
| 2004/0170285 A1 | 9/2004 | Baekgaard et al. |
| 2006/0169529 A1 | 8/2006 | Tamakoshi |
| 2006/0221902 A1 | 10/2006 | Chen |
| 2007/0113649 A1 | 5/2007 | Bharti et al. |
| 2007/0113654 A1 | 5/2007 | Carim |
| 2008/0013747 A1 | 1/2008 | Tran |
| 2008/0175406 A1 | 7/2008 | Smith |
| 2008/0232604 A1 | 9/2008 | Dufresne et al. |
| 2008/0232605 A1 | 9/2008 | Bagha |
| 2008/0273709 A1 | 11/2008 | Thiagarajan |
| 2008/0298603 A1 | 12/2008 | Smith |
| 2009/0213264 A1 | 8/2009 | Kim |
| 2010/0056956 A1 | 3/2010 | Dufrense |
| 2010/0167646 A1 | 7/2010 | Alameh |
| 2011/0190665 A1 | 8/2011 | Bedingham |
| 2014/0107515 A1 | 4/2014 | Lee |

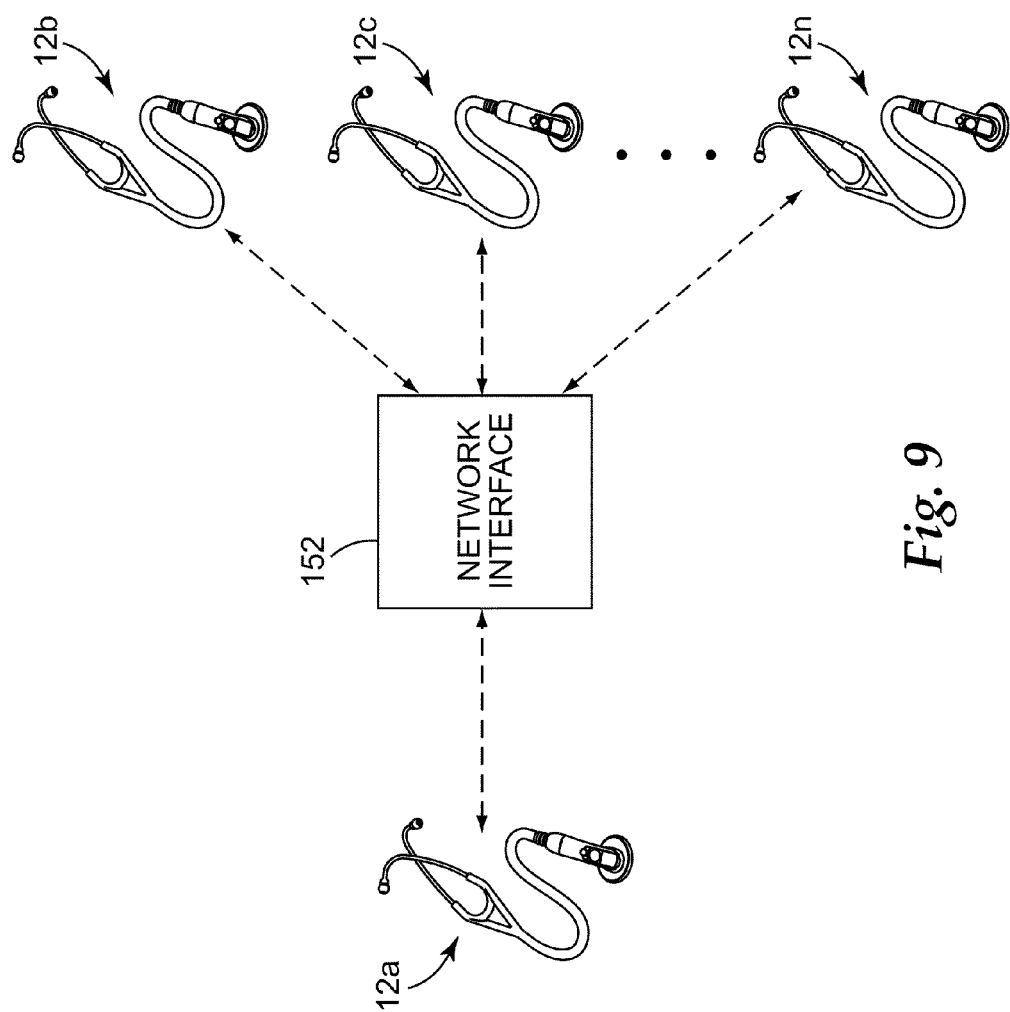

ELECTRONIC STETHOSCOPE SYSTEM FOR TELEMEDICINE APPLICATIONS

CROSS REFERENCE TO RELATED APPLICATIONS

This application claims the benefit of Provisional Application No. 61/300,285, filed Feb. 1, 2010 and International Application No. PCT/US2010/048745, filed Sep. 14, 2010, both hereby incorporated by reference in their entirety.

BACKGROUND

The present invention relates to telemedicine systems. More specifically, the present invention relates to electronic stethoscopes that transmit signals over a telemedicine system in substantial real-time via a secure digital network.

A variety of devices have been developed to detect sounds produced by the body, such as heart and lung sounds. Known devices range from primarily mechanical devices, such as a stethoscope, to various electronic devices, such as microphones and transducers. The stethoscope, for example, is a fundamental tool used in the diagnosis of diseases and conditions of the cardiovascular system. It serves as the most commonly employed technique for diagnosis of such diseases and conditions in primary health care and in circumstances where sophisticated medical equipment is not available, such as remote areas.

Clinicians readily appreciate that detecting relevant cardiac symptoms and forming a diagnosis based on sounds heard through the stethoscope, for example, is a skill that can take years to acquire and refine. The task of acoustically detecting abnormal cardiac activity is complicated by the fact that heart sounds are often separated from one another by very short periods of time, and that signals characterizing cardiac disorders are often less audible than normal heart sounds.

SUMMARY

In one aspect, the present invention relates to a telemedicine system including a first electronic stethoscope comprising a housing configured for hand-held manipulation, a transducer that senses auscultation signals at a first location, and a headset that delivers audio corresponding to the auscultation signals through earpieces on the headset. The telemedicine system further includes a second electronic stethoscope comprising a housing configured for hand-held manipulation, a transducer, and a headset that delivers audio through earpieces on the headset. The first electronic stethoscope includes a processor that converts the auscultation signals to digital signals representative of the auscultation signals, and an antenna to wirelessly transmit the digital signals to a second location via a secure digital network. The second electronic stethoscope includes an antenna that receives the digital signals representative of the auscultation signals at the second location via the secure digital network, and a processor that converts the digital signals to audio corresponding to the auscultation signals and delivers the audio through earpieces on the headset of the second electronic stethoscope in substantial real time with the sensing of the auscultation sounds at the first location.

In another aspect, the present invention relates to an electronic stethoscope including a housing configured for hand-held manipulation, a transducer supported by the housing and configured to sense auscultation signals at a first location, and a headset coupled to the housing and configured to deliver audio corresponding to the auscultation signals through earpieces on the headset. The electronic stethoscope further includes a processor disposed in the housing and configured to convert the auscultation signals to first digital signals representative of the auscultation signals and to wirelessly transmit the first digital signals from the electronic stethoscope via a secure digital network to a second location such that the audio corresponding to the auscultation signals is provided to headsets of one or more remote electronic stethoscopes at the second location in substantial real time with the sensing of the auscultation sounds at the first location.

In a further aspect, the present invention relates to a telemedicine system including a local electronic stethoscope configured to sense auscultation signals from a patient and convert the auscultation signals to digital signals representative of the auscultation signals. The telemedicine system further includes one or more additional electronic stethoscopes, and a secure network interface connecting the local electronic stethoscope to the one or more additional electronic stethoscopes via a secure digital network. Each of the one or more additional electronic stethoscopes is configured to receive the digital signals representative of the auscultation signals via the secure digital network and to convert the digital signals to audio corresponding to the auscultation signals. The audio is delivered through earpieces on a headset of each of the one or more additional electronic stethoscopes in substantial real time with the sensing of the auscultation sounds by the local electronic stethoscope.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 9 is a diagrammatic view of a telemedicine system according to another embodiment of the present invention.

Figure 1:
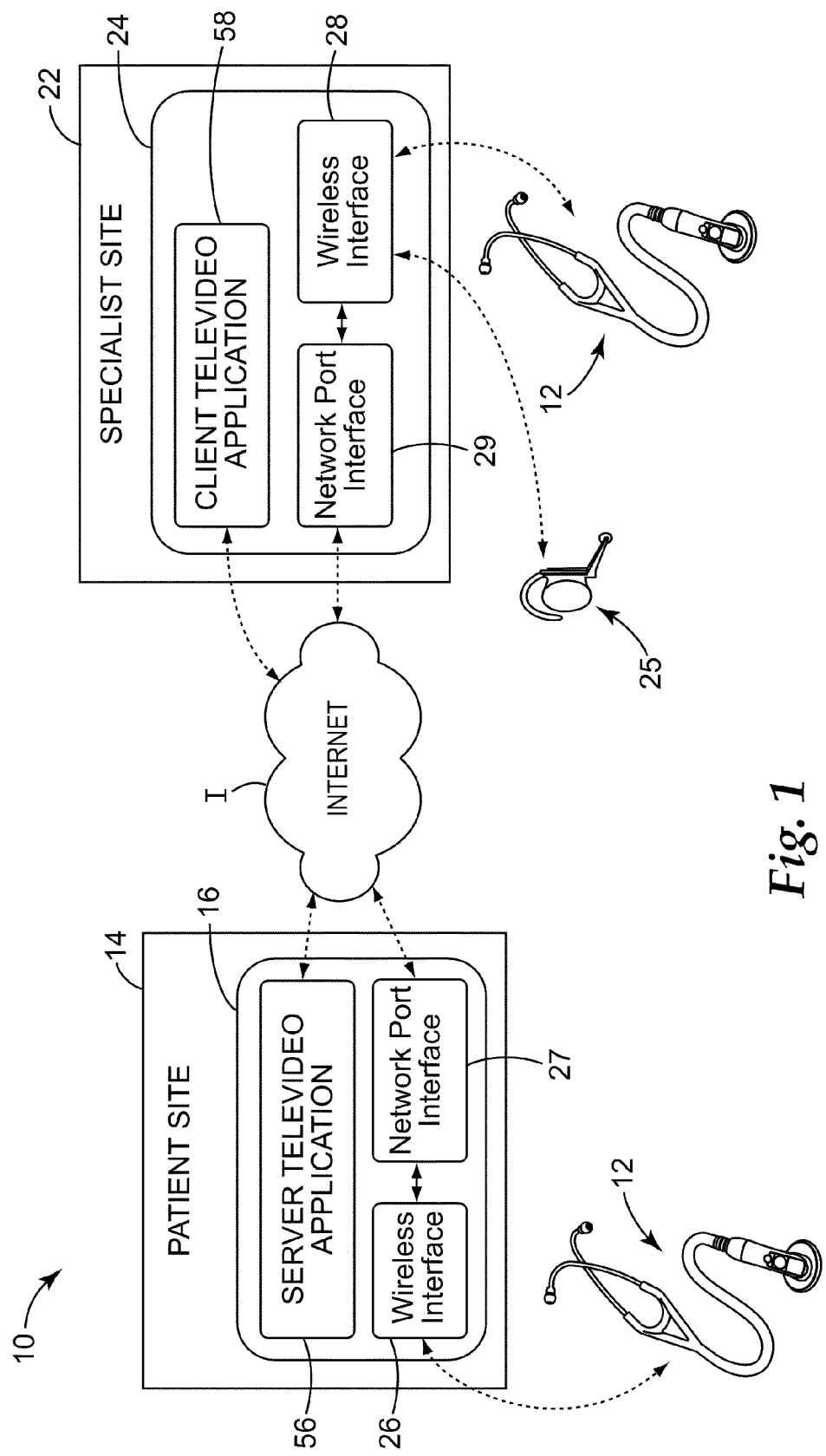
FIG. 1 is a diagrammatic view of a telemedicine system according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a diagrammatic view of an embodiment of a telemedicine system 10 including bioacoustic sensors 12, a patient site computer 14, a patient site software interface 16, a specialist site computer 22, and a specialist site software interface 24. An optional wireless headset 25 is also shown at the specialist site. The patient site bioacoustic sensor 12 communicates with the patient site computer 14 wirelessly, and interacts with the patient site computer 14 via the patient site software interface 16. The specialist site bioacoustic sensor 12 communicates with the specialist site computer 22 wirelessly, and interacts with the specialist site computer 22 via the specialist site software interface 24. The patient site software interface includes a wireless interface 26 and a network port interface 27, and the specialist site software interface includes a wireless interface 28 and a network port interface 29. The patient site computer 14 and the specialist site computer 22 communicate with each other over the Internet I. In short, the bioacoustic sensors 12 communicate with each other via the patient site computer 14, the specialist site computer 22, and the Internet I to allow a clinician or other medical specialist located remotely from the patient site to hear body sounds sensed from a patient at the patient site in substantial real-time. The transmission is in "substantial real-time" due to any delays resulting from signal processing and transmission between the patient and specialist site stethoscopes. Other sounds and information, such as voice signals, may also be transmitted in substantial real-time between the bioacoustic sensors 12.

Figure 2:
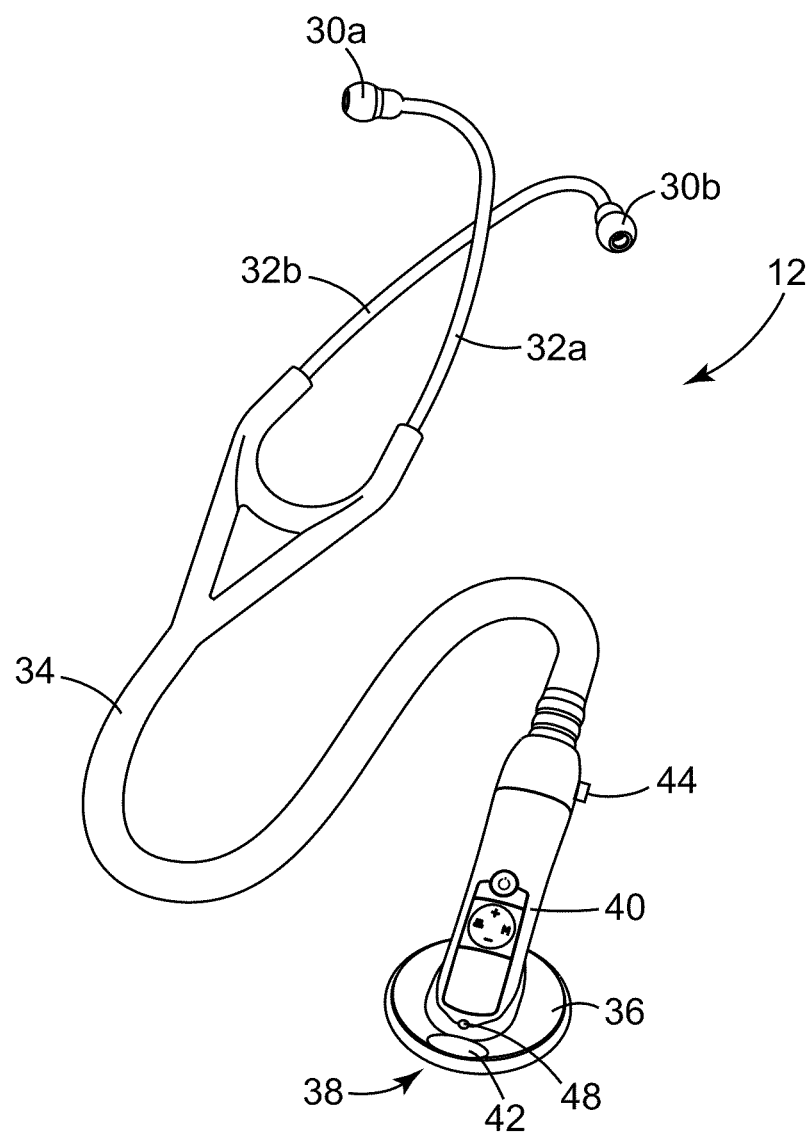
FIG. 2 is a perspective view of an embodiment of an electronic stethoscope suitable for use in the telemedicine system shown in FIG. 1.

FIG. 2 is a perspective view of one embodiment of a bioacoustic sensor, an electronic stethoscope 12, suitable for use in the telemedicine system 10. The electronic stethoscope 12 includes ear tips 30a, 30b, ear tubes 32a, 32b, and a main tube 34. The main tube 34 is coupled to a main housing or chestpiece 36, which supports at least one sensor 38 (not visible in FIG. 2). The sensor 38 is configured to sense sounds produced by matter of biological origin, such as sounds produced by the heart, lungs, vocal cords, or other organs or tissues of the body. In certain embodiments, the sensor 38 may be used to pick up voice sounds from the user of the electronic stethoscope 12 at the patient and/or specialist sites. Other components that may be disposed in or on the main housing 36 include a power source, a microprocessor, signal processing circuitry (e.g., a digital signal processor), a keypad, a graphical user interface, and a communications device (e.g., a radio). In addition, the main housing 36 may include power management circuitry such as that described in U.S. Patent Application Publication No. 2008/0232604, entitled "Power Management for Medical Sensing Devices Employing Multiple Sensor Signal Feature Detection," which is incorporated herein by reference in its entirety.

The signal processing circuitry of the electronic stethoscope 12 may be configured to perform a variety of functions, ranging from simple to complex. For example, the signal processing circuitry may be configured to perform relatively sophisticated analysis of bioacoustic signals received from the sensor 38, such as body sound profile matching. The signal processing circuitry may perform various forms of statistical analysis on signals produced by the sensor 38. In such configurations, the signal processing circuitry may include a digital signal processor (DSP). As a further example, the signal processing circuitry may perform selective frequency filtering to enhance different types of body sounds sensed by the electronic stethoscope 12. The signal processing circuitry is further configured to convert the signals generated by the sensor 38 to acoustic signals for transmission through the ear tubes 32a, 32b for accurate and faithful reproduction of the body sounds through the ear tips 30a, 30b. In some embodiments, the electronic stethoscope 12 is configured to generate acoustic signals as described in U.S. Pat. No. 6,134,331, entitled "Electronic Stethoscope," U.S. Pat. No. 7,006,638, entitled "Electronic Stethoscope," and/or U.S. Pat. No. 7,130,429, entitled "Method and an Apparatus for Processing Auscultation Signals," each of which is incorporated by reference in its entirety.

In some embodiments, the sensor 38 of the electronic stethoscope is configured to modulate or generate an electrical signal in response to deformation of the transducer. Suitable transducers are those that incorporate piezoelectric material (organic and/or inorganic piezoelectric material) such as piezoelectric film, piezoresistive material, strain gauges, capacitive or inductive elements, a linear variable differential transformer, and other materials or elements that modulate or generate an electrical signal in response to deformation. The sensor 38 may be planar or non-planar, such as in the case of a curved or corrugated configuration. Suitable piezo materials may include polymer films, polymer foams, ceramic, composite materials or combinations thereof. The sensor 38 may incorporate arrays of transducers of the same or different transducer type and/or different transducer materials, all of which may be connected in series, individually, or in a multi-layered structure. Suitable transducers that incorporate plural sensing elements having differing characteristics and/or sensors with tailorable sensing characteristics are disclosed in commonly owned U.S. Patent Application Publication Nos. 2007/0113649 and 2007/0113654, each of which is incorporated herein by reference in its entirety.

The sensor 38 may be implemented using technologies other than those that employ electromagnetic energy or piezo materials. For example, the sound to be transduced may move a cantilever that has a highly reflective surface, and a laser or optical beam of light shining on this surface may be modulated. The intensity or other property of the modulated light may be received by a photodetector that outputs an electrical signal for analysis. As a further example, one or more accelerometers may be employed to sense sound signals and produce electrical signals corresponding to the sound signals.

The electronic stethoscope 12 also includes a user interface 40. The user interface 40 may include a number of mode and/or status indicators and mode and/or control switches. The switches may include volume or gain control switches and mode selection switches, for example. The indicators may provide an indication of a selected filter mode, or other information, such as battery and communication link status. Such communication link status indication may be based on the error detection (e.g., CRC and other methods described below) performed by a computer 14, 22 and/or the electronic stethoscope 12 at the patient or specialist site. In preferred embodiments, only the occurrence of an error, and not the lack thereof, is reported. For example, if errors are identified by either the specialist site computer 22 and/or the specialist site electronic stethoscope 12, the specialist site electronic stethoscope 12 may send a signal to the specialist site computer 22 that the data received by the specialist site electronic stethoscope 12 is not the same as the data sent by the patient site electronic stethoscope 12. The indication may then be provided by the user interface 40, which shows the clinician at the specialist site that the sound being heard through the specialist site electronic stethoscope 12 is not a faithful reproduction of the body sound signals sensed by the patient site electronic stethoscope 12. As used herein, the term "faithful reproduction" means a digitally exact replica.

The electronic stethoscope 12 also includes an integrated communications system to communicate signals wirelessly with the patient site computer 14 or the specialist site computer 22. Information acquired by the electronic stethoscope 12 during auscultation, for example, may be transmitted to the computer 14, 22. The computer 14, 22 may process the information to provide various output data, such as a visual, graphical and/or audible representation of the information (e.g., heart rate indication, S1-S4 heart sounds), and/or diagnostic information regarding anomalous cardiac, lung, or other organ function (e.g., phonocardiogram, frequency spectrogram, cardiac murmurs such as those resulting from valve regurgitation or stenosis, breathing disorders such as pneumonia or pulmonary edema), or other organ pathology.

The communications system may be used to establish a radio frequency (RF) communication link between the electronic stethoscope 12 and the computer 14 or 22 or other external device (e.g., personal computer, personal digital assistant (PDA), cell phone, netbook, etc.), as will be described in more detail below. The communication link may be implemented using a short-range wireless communication interface, such as an interface conforming to a known communications standard, such as a Bluetooth standard, IEEE 802 standards (e.g., IEEE 802.11), a ZigBee or similar specification, such as those based on the IEEE 802.15.4 standard, or other public or proprietary wireless protocol. For example, in some embodiments, the communications system is a Class 1 or Class 2 Bluetooth radio. Wireless communication may be implemented in manners that utilize one or several of the following energy forms: electromagnetic radiation, optical (including near infrared), and acoustic (including high frequency beyond average hearing limit). In some embodiments, the communications system is employed to establish a secure communications link between the electronic stethoscope 12 and the computer.

In some embodiments, an antenna (not shown) for the wireless communications system is integrated into the main housing 36. In order to improve the communication link with the electronic stethoscope 12, an aperture 42 may be formed in the metal main housing 36 and covered with a more electromagnetically transparent material. For example, the aperture 42 can be covered with a polymeric member. A flashing light source (e.g., LED) may be mounted in the aperture 42 to indicate that the connection between the electronic stethoscope 12 and the computer is active, and to remind the user of the electronic stethoscope 12 to not cover the aperture 42. A return signal strength indicator may be included on the user interface 40 to provide the strength of the communication link to the user while a connection with the computer is established. In some embodiments, a small parabolic reflector is placed under the antenna to reflect signals transmitted from the antenna normally lost into the tissue of the patient, and to concentrate signals received from the computer captured by the antenna. In an alternative embodiment, the antenna is mounted in one of the ear tubes 32a, 32b or the main tube 34 to locate the antenna higher and improve the line-of-sight with the computer. The antenna may include multiple branches that are mountable on both sides of the ear tubes 32a, 32b to allow unobstructed signal communication under varying body orientations.

The electronic stethoscope 12 may also include a wired connection port 44 to allow for a wired connection between the electronic stethoscope 12 and the computer 14 or 22 or other external device (e.g., personal computer, personal digital assistant (PDA), cell phone, netbook, etc.). A conductor (electrical or optical) may be connected between the wired connection port 44 of the electronic stethoscope 12 and an appropriate connector on the external device. The wired connection port 44 of the electronic stethoscope 12, and any necessary interface circuitry, may be configured to communicate information in accordance with a variety of protocols, such as FireWire™ (IEEE 1394), USB, Mini USB, or other communications protocol. In addition, the connection port 44 may be configured to connect to a docking station that interfaces the electronic stethoscope 12 with the computer 14 or 22. The attachment of the electronic stethoscope 12 to the cable or docking station can trigger the automatic launch of control/application software on the computer 14 or 22 and/or allow sound or data files stored on the electronic stethoscope 12 to upload or synchronize into the computer 14 or 22. When connected, recharging power may also be delivered to the electronic stethoscope 12 via the wired connection port 44.

An acoustic transducer or microphone 48 may also be integrated into the top side (i.e., the side facing away from the sensor 38) of the main housing 36. The microphone 48 may be used to receive ambient sounds from the area surrounding the microphone 48. For example, the microphone 48 may be used, in addition to or in lieu of sensor 38, to pick up voice sounds from the user of the electronic stethoscope 12 at the patient and/or specialist sites.

In some embodiments, the electronic stethoscope 12 includes an integrated electronic storage medium that allows a user to store voice tracks, body sounds, or other recordings in the electronic stethoscope 12 for later review. The electronic storage medium may further include voice recognition data to identify the user or owner of the stethoscope and speech recognition data to identify voice commands so that certain settings (e.g., power, volume) of the electronic stethoscope 12 may be modified in response to voice commands. Speech recognition voice commands may also be used to transfer voice tracks, body sounds, or other recordings or files to a patient medical record database. In some embodiments, the electronic stethoscope is configured to transcribe the content of voice signals into records or other data files (e.g., patient medical records), as described, for example, in U.S. Pat. No. 7,444,285 (Forbes). The voice tracks may also be stored with sound tracks relating to sensed body sounds such that the body sounds and voice tracks can be played back simultaneously through the ear tips 30a, 30b. In some embodiments, the user interface 40 allows the user to scroll through the body sounds and voice tracks stored in the electronic storage medium for selection and playback. The microphone 48 may also be employed for active ambient noise reduction to remove unwanted surrounding environmental noise from the recorded body and voice signal.

Referring back to FIG. 1, the electronic stethoscope 12 at the patient site may be linked to or paired with the patient site computer 14 via the secure wireless interface 26 to establish a secure network connection between the patient site electronic stethoscope 12 and the patient site computer 14. Similarly, the electronic stethoscope 12 at the specialist site may be linked to or paired with the specialist site computer 22 via the secure wireless interface 28 to establish a secure network connection between the specialist site electronic stethoscope 12 and the specialist site computer 22. While a single electronic stethoscope 12 is shown at each of the patient and specialist sites, it will be appreciated that a plurality of electronic stethoscopes 12 may be linked to the patient site computer 14 and/or the specialist site computer 22. In some embodiments, the electronic stethoscopes 12 are paired with their respective computers 14, 22 via a personal area network (PAN). One example of a PAN is a Bluetooth network, in which a pairing code is established on one of the electronic stethoscope 12 and computer 14 or 22, and entered on the other of the electronic stethoscope 12 and computer 14 or 22. In some embodiments, the optional wireless headset 26 is also linked to or paired with the specialist site computer 22 via the secure wireless interface 28.

A secure connection is also established between the network port interfaces 27, 29 of computers 14, 22, respectively, over the Internet I such that the electronic stethoscopes 12 can communicate with each other over a secure network connection. For example, the network port interfaces 27, 29 may exchange certificates, require authentication, or establish secure network keys to establish a secure connection. The data may also be encrypted by the computers 14, 22 prior to sending the data over the Internet I. The secure network key may then be employed to decrypt the data when received. In some embodiments, the network port interfaces 27, 29 allow applications on the computers 14 and 22 to interface with the wireless interfaces 26, 28 remotely across the Internet I.

In an alternative embodiment, the electronic stethoscopes 12 are configured to communicate with each other directly via a secure connection (i.e., without interfacing with the computers 14 and 22). For example, each electronic stethoscope 12 may be configured with a unique Internet Protocol (IP) address, and the electronic stethoscopes 12 may establish a secure connection with each other directly using a wireless fidelity (WiFi) connection or other wireless connection. As another example, the patient site and/or specialist site may include a plurality of electronic stethoscopes 12 that communicate with each other locally.

When the electronic stethoscopes 12 are linked over a secure network connection, signals may be sent between the electronic stethoscopes 12, or between the electronic stethoscopes 12 and the computers 14, 22, in substantial real-time. For example, body sounds may be transmitted from the electronic stethoscope at the patient site to the ear tips 30a, 30b at the specialist site in substantial real-time. The body sounds may also be reproduced in substantial real-time by speakers connected to the computers 14, 22. In some embodiments, the electronic stethoscopes 12 at the patient and specialist sites are substantially identical such that the body and other sounds are reproduced substantially identically in the ear tips 30a, 30b at the patient site and the specialist site. In addition, sounds may be recorded and stored by one of the electronic stethoscopes 12 and later played (either from the memory in the electronic stethoscope 12 or from one of the computers 14, 22) at substantially the same time to all networked electronic stethoscopes 12. In some embodiments, the signals transmitted by the patient site electronic stethoscope 12 to the patient site computer 14 and over the Internet I are packetized and enumerated by the patient site electronic stethoscope 12, and undergo an error check at the specialist site to assure faithful sound quality and reliable reproduction at the specialist site electronic stethoscope 12. The error check may be performed by each element of the telemedicine system 10 (i.e., patient site computer 14, specialist site computer 22, and specialist site electronic stethoscope 12) as a further assurance of accurate transmission of data from the patient site electronic stethoscope 12. The error check may be any use suitable data transmission check techniques, including, but not limited to, cyclic redundancy check (CRC), checksum, horizontal and vertical redundancy check, hash function, repetition code, and the like. The system may also incorporate, for example, sample throughput measurements, performed to determine excess data or data starvation in the communication link. In short, the sound packets from the patient site electronic stethoscope 12 are directly relayed (i.e., mirrored) over the Internet I to the specialist site electronic stethoscope 12.

In preferred embodiments, the telemedicine system 10 includes an error check and validation independent of the underlying communication system or network (e.g., Bluetooth, TCP/IP) protocol. The independent error check may be performed at any component of the telemedicine system 10 as a further assurance that the signal is a faithful reproduction of the auscultation sounds from the patient site electronic stethoscope 12. In certain preferred embodiments, interruptions in service of the underlying system are classified according to duration and severity, with all errors resulting in a communication to the user (via one or more components of the telemedicine system) that the signal is not a faithful reproduction. For example, a patient site component may send a packetized or other signal to a specialist site system component every other 500 milliseconds. An interruption in the underlying communication system or network exceeding 500 milliseconds may result in a dropped packet/signal and a resultant indication at the specialist site of degraded sound quality (e.g., via changing color of an indicator).

In addition, ambient sounds, such as voice signals, can be received by the sensor 38 and transmitted between the electronic stethoscopes 12 in substantial real-time, simultaneously or alternatingly with the body sounds. In alternative embodiments, the electronic stethoscopes 12 can receive voice communications and other ambient sounds through the microphone 48 that are processed and communicated to the remote site. The body sound information is continuously streamed from the patient site electronic stethoscope 12 to the specialist site electronic stethoscope 12, while the ambient sounds are streamed in both directions between the patent and specialist site electronic stethoscopes 12. The patient site electronic stethoscope 12, specialist site electronic stethoscope 12, patient site computer 14, and specialist site computer 22 may each include one or more ring buffers to assure a continuous stream of information between the electronic stethoscopes 12. In some embodiments, the ambient sounds are μ-law encoded and superimposed over the body sounds generated by the electronic stethoscope 12 at the patient site. Thus, the clinician at the patient site can hear the body sounds from the patient while receiving voice instructions from the specialist at the specialist site, for example. This allows the specialist at the specialist site to have a substantially hands-on experience with the patient. Because the clinician at the patient site receives the sound through the ear tips 30a, 30b, the clinician at the patient site and the specialist at the specialist site can consult privately, rather than having the specialist site communications output through speakers attached to the patient site computer 14, for example. Signal processing may be employed to optimize the sound quality of the voice signals provided through the ear tips 30a, 30b.

The voice and auscultations sounds reproduced through the ear tips 30a, 30b of the electronic stethoscopes 12 at the patient and specialist sites may be controlled locally at each electronic stethoscope 12. The auscultation and voice signals may be provided to the ear tips 30a, 30b simultaneously, but on separate channels, allowing the clinician to separately control the volume of the auscultation sounds and voice communications. This allows the clinician to optimize the relative volumes of the auscultation and ambient sounds, providing the clinician with a balanced output to the ear tips 30a, 30b that is tailored to the clinician's preferences. Each electronic stethoscope 12 may further include selectable voice enhancement filters that, for example, enhance certain frequency bands of the voice signals to assist with ambient noise reduction.

In some embodiments, the transmission of voice signals is selectably controlled while the stethoscopes are linked over the secure network connection. For example, when connected, the body sounds may be constantly transmitted from the patient site to the specialist site, while the voice signals and other ambient sounds are transmitted between the sites only when the clinician chooses to have the voice signals transmitted. For example, in some embodiments the electronic stethoscope 12 utilizes selective frequency filtering during auscultation to suppress frequency bands characteristic of voice signals. In such embodiments, the clinician may initiate the transmission of voice signals by essentially deactivating the frequency filtering or modifying the filter settings (i.e., allowing reproduction and transmission of only certain frequency bands characteristic of voice signals). In some embodiments, transmission of the voice signals is initiated when the clinician presses a button on the user interface 40. The electronic stethoscope 12 may be configured such that the voice signals are transmitted when the button on the user interface 40 is pressed and held (similar to a handheld transceiver or walkie-talkie). The electronic stethoscope 12 may alternatively be configured such that a voice signal transmission mode is activated when the button is pressed and released, and the voice signal transmission mode is deactivated when the button is subsequently pressed and released again.

The electronic stethoscopes 12 may include an integrated software memory that initially stores the software for the patient site software interface 16 and/or the specialist site software interface 24. For example, the software may be included in each electronic stethoscope 12 when the electronic stethoscope 12 is sold to a consumer. When the electronic stethoscope 12 is paired with the computer 14 or 22, the electronic stethoscope 12 may be configured to automatically load software stored in the software memory onto the computer 14 or 22. When the software is installed on the computers 14, 22, the software allows the electronic stethoscopes 12 to interact with the computers 14, 22, such as by sending information and signals from the electronic stethoscopes 12 to the computers 14, 22 and providing control signals from the computers 14, 22 to the electronic stethoscopes 12.

Also shown in FIG. 1 is a patient site televideo application 56 and server site televideo application 58. In some embodiments, a video camera is connected to the patient site computer 14 and/or the specialist site computer 22 to allow video communications between the patient site and the specialist site via the televideo applications 56 and 58. This allows, for example, the specialist at the specialist site to see the positioning of the sensor 38 relative to the patient at the patient site and to provide feedback to the patient site about the positioning of the sensor 38. As another example, the video cameras may be used in conjunction with the microphones 48 on each of the electronic stethoscopes 12 to provide video conferencing between the patient site and specialist site.

Figure 3:
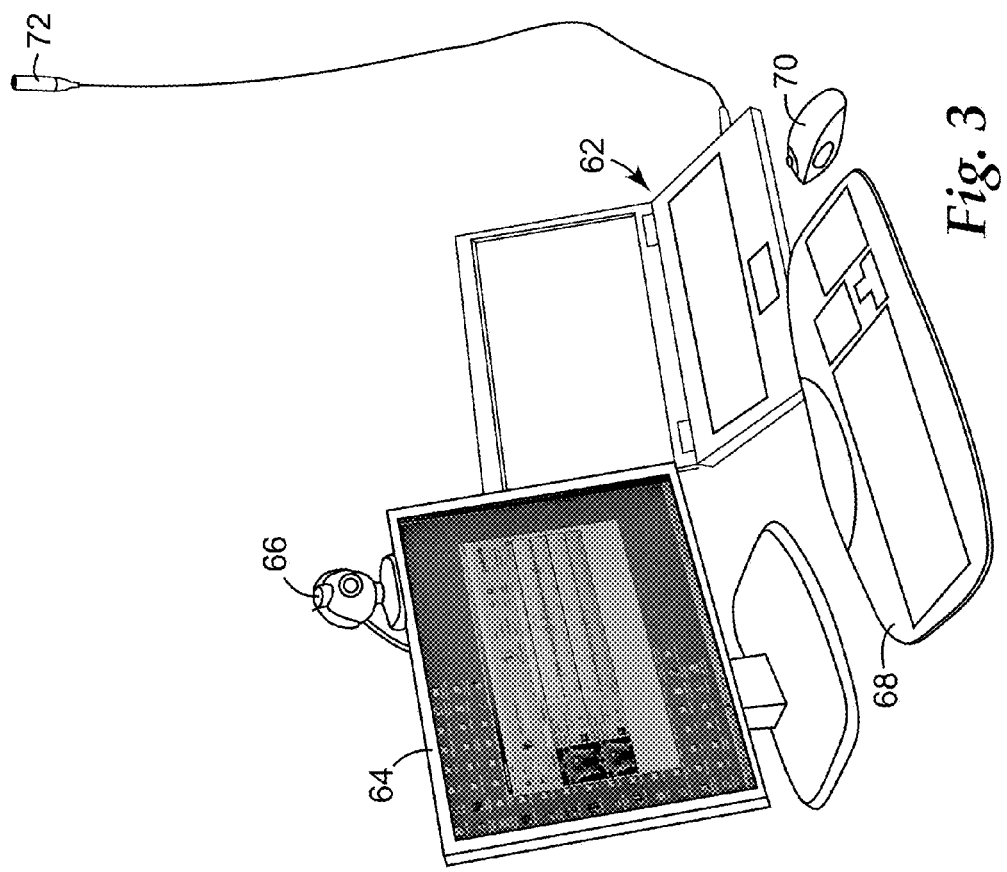
FIG. 3 is a front view of an embodiment of a system for interfacing with an electronic stethoscope at a patient or specialist site.

FIG. 3 is a front perspective view of an embodiment of a computer 60 that is suitable for use as patient site computer 14 and/or specialist site computer 22. The computer 60 includes a processor 62, a display 64, a camera 66, a keyboard 68, a mouse 70, and a communications adapter 72. The processor 62 is also configured for connection to the Internet to facilitate communications between the patient site and the specialist site. The processor 62 is shown as a laptop computer, but the processor may alternatively be a desktop computer or have any other form. In addition, while a separate display 64 is shown, the display of the laptop computer may also be used. Furthermore, other input devices (e.g., trackball, joystick, etc.) may be integrated into the computer 60 for use in the telemedicine system 10.

The processor 62 receives input control signals from the keyboard 68 and mouse 70, and provides video signals to the display 64. In addition, the processor 62 sends signals to and receives signals from the electronic stethoscope 12 via the communications adapter 72. In some embodiments, the communications adapter 72 is a Bluetooth dongle suitable for short-range (e.g., up to 10 m) and medium-range (e.g., up to 100 m) secure communications. The keyboard 68 and the mouse 70 may be used to establish a security code or the like to initiate a secure connection with the electronic stethoscope 12 as described above. The communications adapter 72 may be positioned high on a wall as is shown to improve the line-of-sight and communications link between the electronic stethoscope 12 and the communications adapter 72.

The camera 66 communicates with the processor 62 to capture video of the patient or specialist site. The processor 62 then interfaces across the Internet I via the televideo application 56 or 58 to provide a live video feed to the patient or specialist site. The camera 66 may be mounted on the top of the display 64 as is shown to provide video communications between the patient and specialist sites as described above. The camera 66 may also be configured for wireless communication with the processor 62 to allow the camera 66 to be moved around the patient or specialist site (e.g., to capture video of location of the sensor 38 on the patient). In some embodiments, the keyboard 68 and/or mouse 70 can be used at one site to control the operation of the camera 66 (e.g., zoom, focus, position, etc) at the other site. This allows, for example, the specialist at the specialist site to control the video being captured at the patient site.

Figure 4:
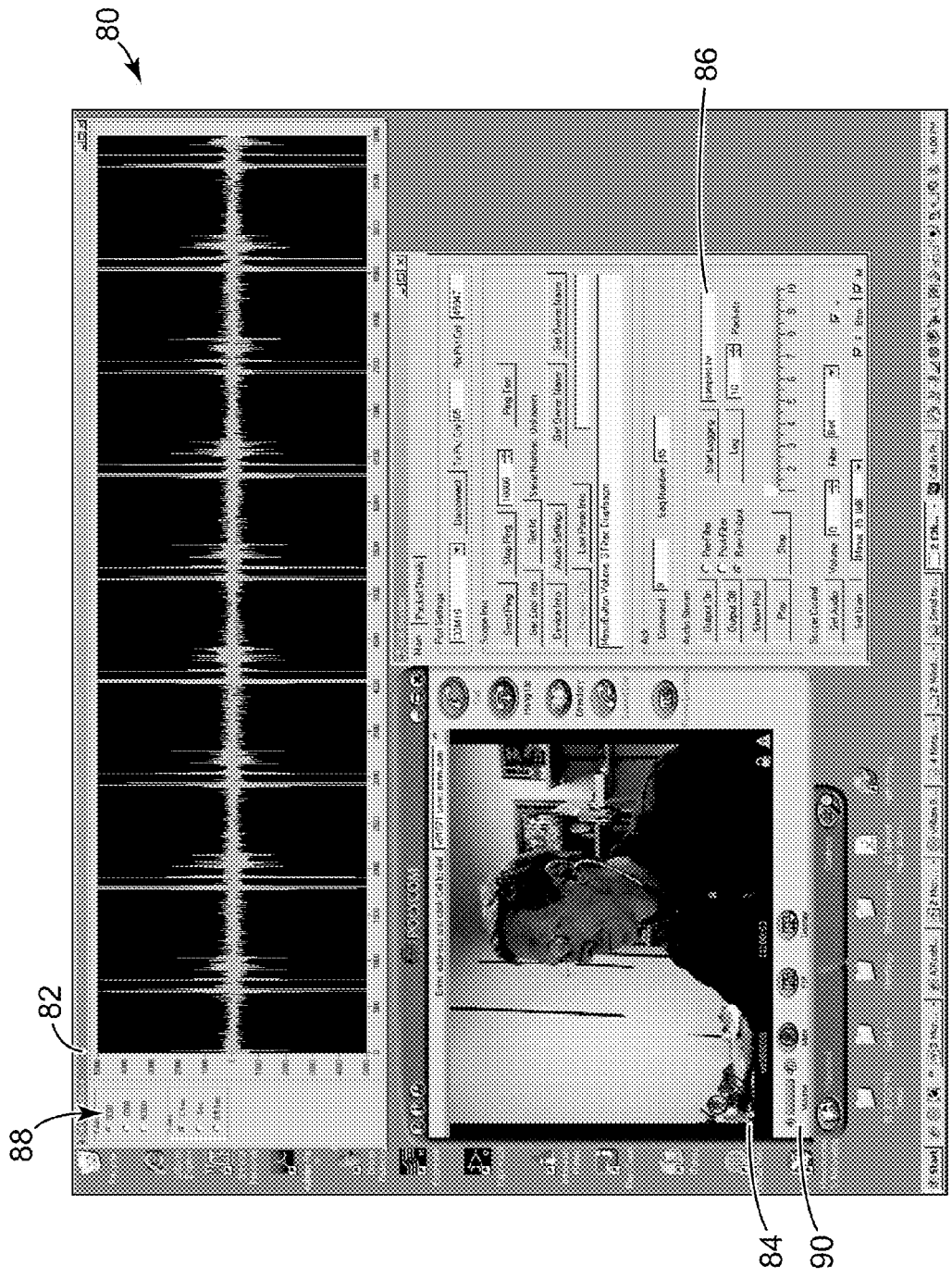
FIG. 4 is a screen shot of an embodiment of a user interface at the patient site.

FIG. 4 is a screen shot of an embodiment of a user interface 80 that may be displayed on the display 64 at the patient site during a telemedicine session. The user interface 80 includes a data display module 82, a video conference module 84, and a stethoscope control module 86. A user of the patient site computer 14 may use the keyboard 68, mouse 70, and/or other input devices to interact with the user interface on the display 64. For example, the user may employ the mouse 70 to select buttons or pull-down menu elements on the user interface 80.

The data display module 82 is a graphical representation of a periodic body sound generated by the patient and sensed by the sensor 38 at the patient site. The signals generated by the sensor 38 are processed by the electronic stethoscope processor and provided to the patient site computer 14 via the integrated antenna. The processor 62 then processes these signals and converts them into appropriate form for display on the data display module 82. The graph can be updated periodically or in substantial real-time while the clinician holds the electronic stethoscope 12 against the patient's body. The scale used or the axes in the graph can be manipulated using the radio buttons 88 on the data display module.

In some embodiments, the electronic stethoscope processor separates the signals generated by the sensor 38 into a plurality of channels. For example, the electronic stethoscope processor may convert the sensed body sounds to data signals representative of the sensed body sounds and send the data signals to the patient site computer 14 on a first channel, and may convert the sensed body sounds to acoustic signals and send the acoustic signals to the ear tips 30a, 30b on a second channel. Alternatively, the signals generated by the sensor 38 may be sent directly to the patient site computer 14 for conversion to data signals for display the processor 62.

The video conference module 84 displays the video being captured by the camera 66 at the specialist site. This allows the clinician at the patient site to see the specialist at the specialist site, and permits the specialist to demonstrate preferred positioning of the sensor 38 relative to the patient at the patient site, for example. The video conference module 84 also includes a toolbar 90 including a variety of videoconferencing controls. For example, the toolbar 90 may include buttons to control the volume of sound received from the specialist site and the positioning of the video conference on the user interface 80. The toolbar 90 may also include interfaces and tools to start and end the video conference.

The stethoscope control module 86 may include a variety of selectable controls and settings for the electronic stethoscope 12 at the patient site. These settings may be chosen to control the modes, volume, power state, recording settings, and the like of the patient site electronic stethoscope 12. In some embodiments, these settings are also selectable via the user interface 40 on the electronic stethoscope 12. The stethoscope control module 86 may also include options for controlling other modules on the user interface 80. The stethoscope control module 86 may further include selectable options for the communication settings between the electronic stethoscope 12 and the patient site computer 14. For example, the stethoscope control module 86 may allow for adjustment of the packetization settings of the electronic stethoscope 12, or to check and repair the connection settings between the electronic stethoscope 12 and the patient site computer 14.

Figure 5:
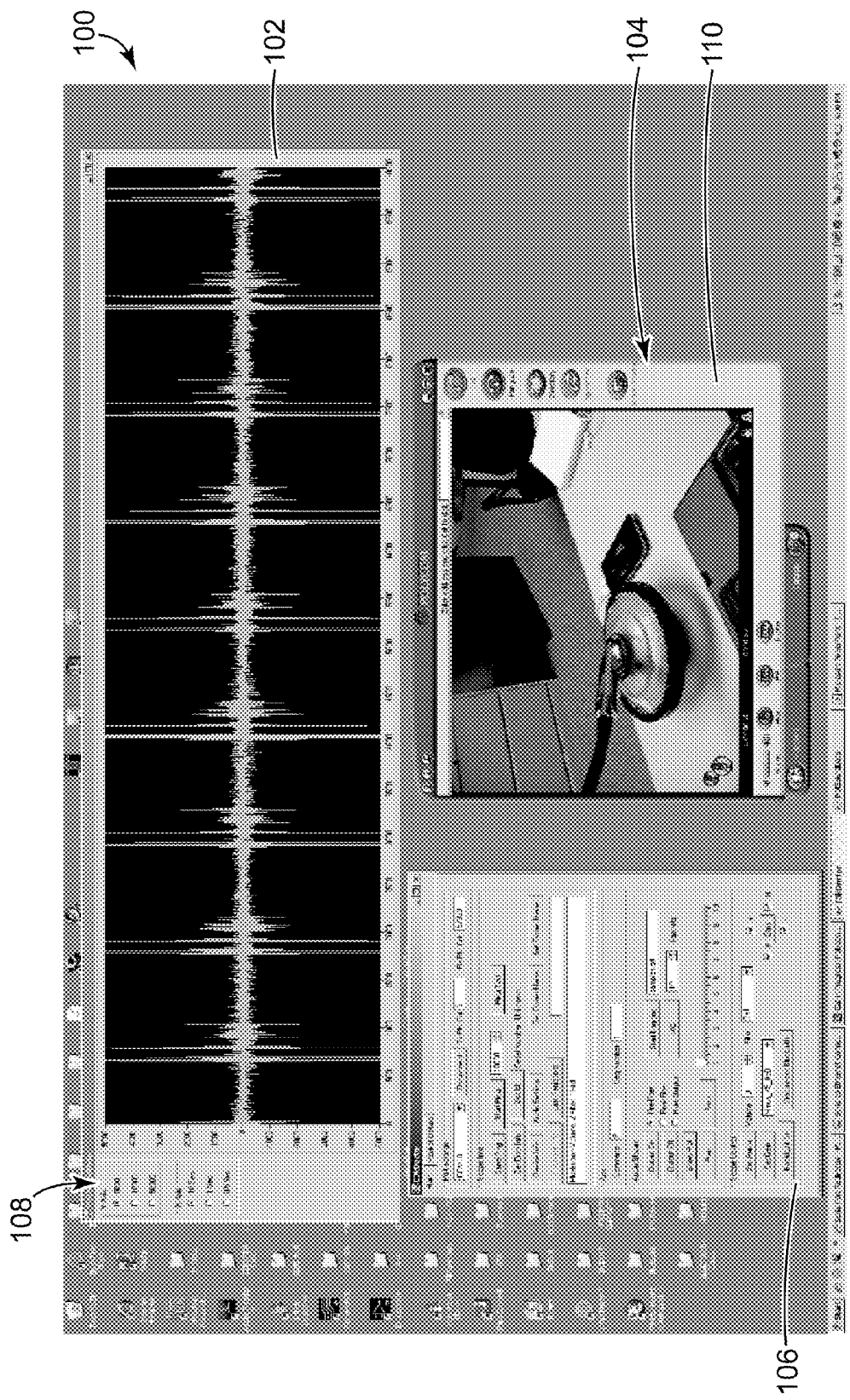
FIG. 5 is a screen shot of an embodiment of a user interface at the specialist site.

FIG. 5 is a screen shot of an embodiment of a user interface 100 that may be displayed on the display 64 at the specialist site during a telemedicine session. Similar to the user interface 80, the user interface 100 includes a data display module 102, a video conference module 104, and a stethoscope control module 106. A user of the specialist site computer 22 may use the keyboard 68, mouse 70, and/or other input devices to interact with the user interface on the display 64. For example, the user may employ the mouse 70 to select buttons or pull-down menu elements on the user interface 100.

The data display module 102 is a graphical representation of a periodic body sound generated by the patient and sensed by the sensor 38 at the patient site. The signals generated by the sensor 38 are processed by the electronic stethoscope processor, provided to the patient site computer 14, and sent to the specialist site computer 22. The specialist site computer processor 62 then processes these signals and converts them into appropriate form for display on the data display module 102. The graph can be updated periodically or in substantial real-time while the clinician at the patient site holds the electronic stethoscope 12 against the patient's body. The scale used or the axes in the graph can be manipulated using the radio buttons 108 on the data display module.

The video conference module 104 displays the video being captured by the camera 66 at the patient site. This allows the specialist at the specialist site to see the positioning of the sensor 38 relative to the patient at the patient site, for example. The video conference module 104 also includes a toolbar 110 including a variety of videoconferencing controls. For example, the toolbar 110 may include buttons to control the volume of sound received from the patient site and the positioning of the video conference on the user interface 100. The toolbar 110 may also include interfaces and tools to start and end the video conference. The toolbar 110 may also include controls to adjust the camera position at the patient site.

The stethoscope control module 106 may include a variety of selectable controls and settings for the electronic stethoscopes 12 at the patient site and/or the specialist site. These settings may be chosen to control the modes, filtering, volume, power state, recording settings, and the like of the patient and/or specialist site electronic stethoscopes 12. For example, the stethoscope control module 106 may include an interface to control the mode and filter settings on patient site electronic stethoscope 12. The stethoscope control module 106 may also be configured to allow control of some settings on the patient site electronic stethoscope 12, while leaving other settings for only local control. For example, the stethoscope control module 106 may provide volume control for only the specialist site electronic stethoscope 12, while the volume for the patient site electronic stethoscope 12 is only controllable at the patient site (e.g., via the stethoscope control module 86 or the user interface 40 on the patient site electronic stethoscope 12). In some embodiments, the specialist site electronic stethoscope 12 may also be configured such that the user interface 40 on the specialist site electronic stethoscope 12 controls settings of the patient site electronic stethoscope 12 when connected over a secure network. The specialist site electronic stethoscope 12 may also be configured to control substantially all of the settings on the patient site electronic stethoscope 12 (i.e., local control at the patient site is essentially disabled), while still allowing the patient site to control of volume. Such local control ensures that volume may be adjusted according to user preference at each location.

In an alternative embodiment, the clinician at the specialist site may set the specialist site electronic stethoscope 12 to the desired settings and subsequently send the settings of the specialist site electronic stethoscope 12 to the patient site electronic stethoscope 12 (e.g., via the specialist site computer 22 and the patient site computer 14) in one transmission to update the settings on the patient site electronic stethoscope 12.

The stethoscope control module 106 may further include selectable options for the communication settings between the patient site electronic stethoscope 12 and the patient site computer 14 and/or the specialist site electronic stethoscope 12 and the specialist site computer 22. For example, the stethoscope control module 106 may allow for adjustment of the packetization settings of the electronic stethoscope 12, or to check and repair the connection settings between the electronic stethoscope 12 and the specialist site computer 22.

Figure 6:
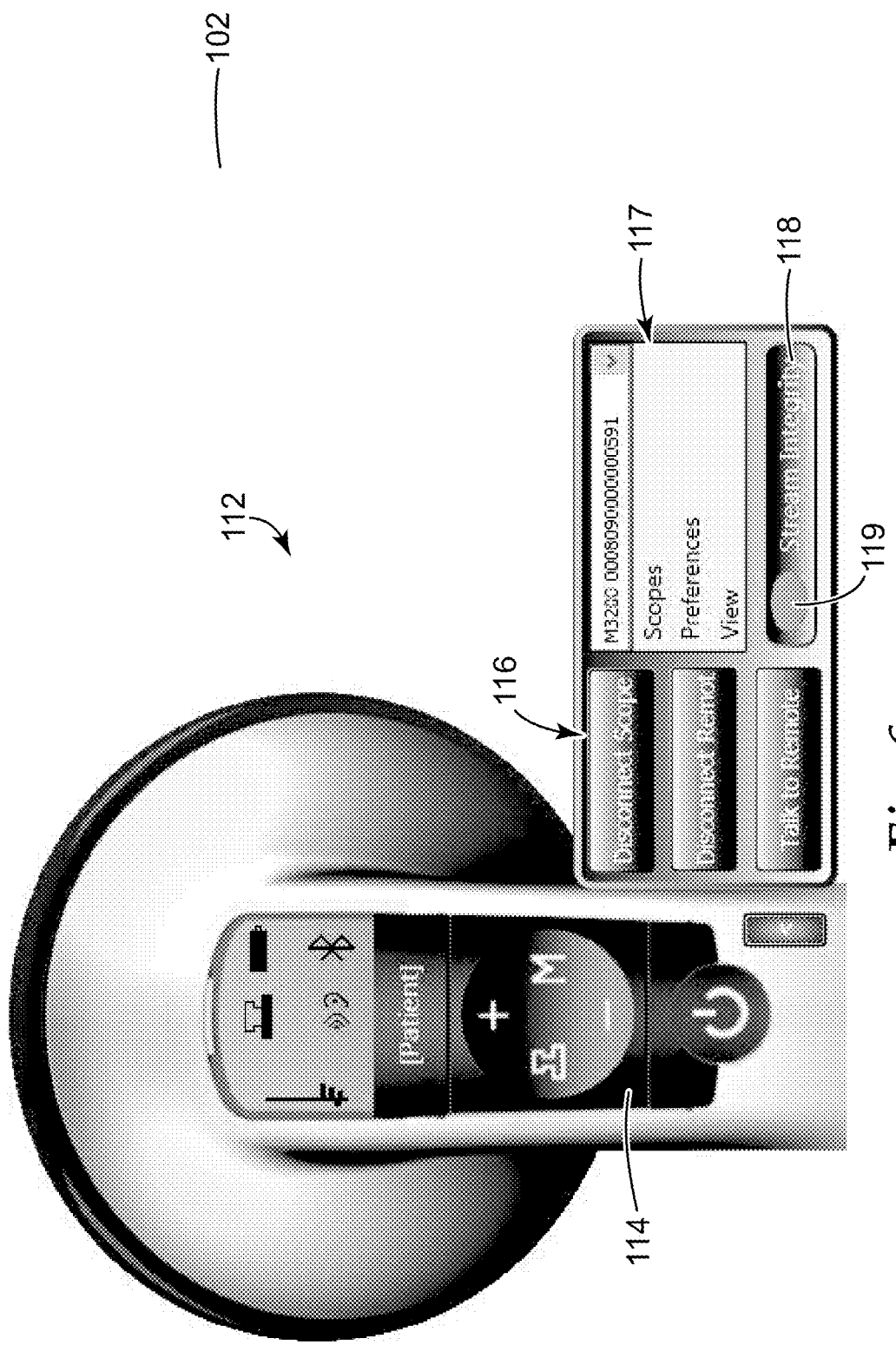
FIG. 6 is a screen shot of a graphical user interface that may be displayed on the user interfaces shown in FIGS. 4 and 5.

The user interface 100 shown and described is merely exemplary and other configurations for the user interface are possible. In one exemplary alternative configuration, shown in FIG. 6, the user interface 100 may include a first graphical user interface 112 that is a feature enhanced image of the housing 36 on the specialist site electronic stethoscope 12, having a control section 114 including each of the buttons and other interfaces on the user interface 40 on the specialist site electronic stethoscope 12. Each button on the control section 114 may be selectable to produce the same function on the specialist site electronic stethoscope 12 as if the corresponding button on the user interface 40 were pressed. A user interface similar to user interface 112 may also be displayed on the user interface 80 to provide on-screen function control for the patient site electronic stethoscope 12.

When the specialist site electronic stethoscope 12 is connected to and synchronized with the patient site electronic stethoscope 12, the user interface 100 may display a single graphical user interface that is a feature enhanced image of the housing 36 on the patient site electronic stethoscope 12, including each the buttons and other interfaces on the user interface 40 on the patient site electronic stethoscope 12. This same graphical user interface 112 may also be displayed on the user interface 80. When the patient and specialist site electronic stethoscopes 12 are connected, each button on the graphical user interface 112 may be selectable at either the patient or specialist site to produce the same function on the patient site electronic stethoscope 12 as if the corresponding button on the user interface 40 of the patient site stethoscope were pressed. The graphical user interface 112 provides the clinician at the specialist site with an interface through which certain settings (e.g., mode, filters, etc.) of the patient site electronic stethoscope 12 are controllable.

The graphical user interface 112 may also include a plurality of connectivity buttons 116 that may be used to control the connection between the specialist site computer and the connected electronic stethoscopes 12. For example, in the embodiment shown in FIG. 6, the connectivity buttons 116 include a "Disconnect Scope" button that allows for disconnection of the local specialist site electronic stethoscope 12 from the specialist site computer 22, a "Disconnect Remote" button that allows for disconnection of the specialist site computer 22 (and desynchronization of the specialist site electronic stethoscope 12) from the patient site electronic stethoscope 12, and a "Talk to Remote" button that activates voice communications between the specialist and patient site electronic stethoscopes 12. When the specialist site electronic stethoscope 12 is not connected to the patient site electronic stethoscope 12, the "Disconnect Remote" and "Talk to Remote" buttons may be inactivated or may not appear on the graphical user interface 112.

Additionally, the graphical user interface 112 may include an options menu 117 that allows the user to control various options associated with the connected electronic stethoscope 12. For example, in the embodiment shown in FIG. 6, the options menu 117 includes a pull-down menu that allows the clinician to scroll between the stethoscopes connected to the specialist site computer 22. This toggles the active electronic stethoscope 12 active on the graphical user interface 112, allowing the clinician to modify the settings for each of the connected stethoscopes.

The graphical user interface 112 may further include a visual and/or audio indication that indicates that the sound heard by the clinician at the specialist site electronic stethoscope 12 is a faithful reproduction of the sound from the patient site electronic stethoscope 12. In the embodiment shown in FIG. 6, the graphical user interface 112 includes a fidelity gauge 118 labeled "Stream Integrity" that includes a fidelity indicator 119. The fidelity indicator 119 changes color to indicate whether faithful sound reproduction is occurring at the specialist site electronic stethoscope 12. For example, the fidelity indicator 119 may be displayed in green when the sound is a faithful reproduction and in red when the sound is not a faithful reproduction. This indication may be based on the error detection (e.g., CRC) performed by the specialist site computer 22 and/or the specialist site electronic stethoscope 12. The error detection may also be performed by the patient site computer 14 and/or patient site electronic stethoscope 12. For example, if errors are identified by either the specialist site computer 22 and/or the specialist site electronic stethoscope 12, the specialist site electronic stethoscope 12 may send a signal to the specialist site computer 22 that the data received by the specialist site electronic stethoscope 12 is not the same as the data sent by the patient site electronic stethoscope 12. The indication may then be provided by the user interface 100, which shows the clinician at the specialist site that the sound being heard through the specialist site electronic stethoscope 12 is not a faithful reproduction of the body sound signals sensed by the patient site electronic stethoscope 12. The specialist site electronic stethoscope 12, the patient site electronic stethoscope 12, and/or the user interface 80 may also provide an indication of faithful sound reproduction. In alternative embodiments, the lack of error is reported to system components.

Figure 7:
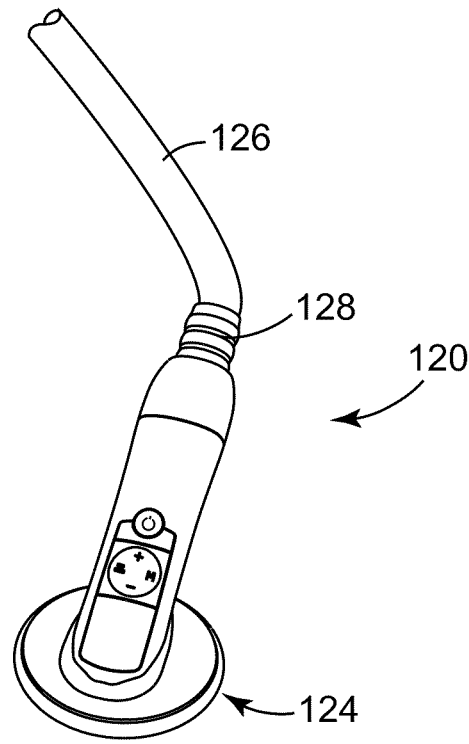
FIG. 7 is a perspective view of an embodiment of a wireless chestpiece for use in the telemedicine system shown in FIG. 1.
Figure 8:
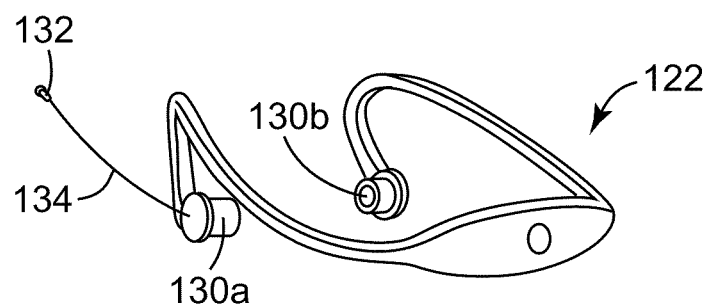
FIG. 8 is a perspective view of an embodiment of a wireless headset for use in the telemedicine system shown in FIG. 1.

While the electronic stethoscope 12 has been described with regard to a stethoscope having a chestpiece, main tube, and binaurals connected to ear tips, the electronic stethoscope used in the telemedicine system 10 may have other configurations. For example, FIG. 7 illustrates a wireless chestpiece 120 and FIG. 8 illustrates a wireless headset 122 usable in association with the telemedicine system 10.

The wireless chestpiece 120 is configured substantially similarly to the chestpiece 36 described above with regard to FIG. 2, and interacts with elements of the telemedicine system 10 in substantially the same way as the electronic stethoscope 12. In particular, the wireless chestpiece 120 is configured to connect with the computers 14, 22 via a secure network connection. Components that may be disposed in the chestpiece 120 include a power source, signal processing circuitry, and a communications interface. A sensor 124 (not shown) is supported at one end of the wireless chestpiece 120, and an antenna 126 is mounted at an end of the wireless chestpiece 120 opposite the sensor 124. In some embodiments (not shown), an antenna is integrated into the housing as described above. The sensor 124 may have properties and configurations similar to those described above with regard to sensor 38. In the embodiment shown, the antenna 126 is configured to swivel or rotate about pivot 128 to allow the antenna 126 to be positioned for maximum signal coupling during use. The antenna 126 can also be positioned to minimize clearance during storage. In some embodiments, the antenna 126 is a high performance antenna for large signal range (e.g., greater than 100 m), thereby maximizing the mobility of the wireless chestpiece 120.

The wireless headset 122 is configured to receive signals from the wireless chestpiece 120 via a secure connection. In some embodiments, the chestpiece 120 and headset 122 are paired with each other via a Bluetooth connection. The wireless headset 122 may also be configured to communicate with the computer 14 or 22, similar to the headset 26 shown in FIG. 1. The wireless headset 122 may have various configurations, including over-the-ear and in-ear designs. In the embodiment shown, the wireless headset 122 includes ear tips 130a, 130b for in-ear use. In some embodiments, the ear tips 130a, 130b are substantially the same as ear tips 30a, 30b in FIG. 2 to provide consistent sound quality to the user between the electronic stethoscope 12 and the wireless headset 122.

The wireless headset 122 may also include a microphone 132 for receiving voice sounds from the user. The microphone 132 is coupled to an adjustable support 134 that allows the microphone 132 to be repositioned relative the user. The signals received by the microphone 132 may be superimposed over the body sounds sensed by the wireless headset 120 and sent over the Internet I, as described above.

In addition to the electronic stethoscope used in the telemedicine system 10 having alternative configurations, the connection between the electronic stethoscopes may also have alternative configurations. For example, FIG. 9 is a diagrammatic view of a telemedicine system 150 according to an alternative embodiment. The telemedicine system 150 include a sensing electronic stethoscope 12a, a plurality of networked electronic stethoscopes 12b, 12c, . . . , 12n, and a network interface or hub 152. The electronic stethoscopes 12a-12n communicated wirelessly with the network interface 152. The electronic stethoscopes 12a-12n may be configured substantially similarly and have substantially similar properties as electronic stethoscope 12 described above in FIG. 2. It will be appreciated that electronic stethoscope 12n is representative of the nth networked electronic stethoscope 12, and should not be construed as limiting or defining the number of networked electronic stethoscopes 12 connected to the network interface 152. In some embodiments, the network interface 152 is configured as a wearable, handheld, or portable device.

The network interface 152 is configured to establish a secure connection with the electronic stethoscopes 12a-12n. In some embodiments, the electronic stethoscopes 12a-12n are paired with the network interface 152 via a personal area network (PAN). One example of a PAN is a Bluetooth network, in which a pairing code is established on the network interface 152 and entered on each electronic stethoscope 12a-12n to securely connect to the network interface 152. When connected, the sensing electronic stethoscope 12a may be used to sense a patient's body sounds, while the networked electronic stethoscopes 12b-12n may be used to listen to the patient body sounds sensed by the sensing electronic stethoscope 12a in substantial real-time. In addition, other sounds, such as voice prompts, may be received on a sensor 38 or microphone 48 of one of the electronic stethoscopes 12a-12n and delivered to each of the networked electronic stethoscopes 12a-12n. In alternative embodiments, the electronic stethoscopes 12a-12n are networked directly to each other (i.e., without interfacing with the intermediate network interface 152).

In one example implementation, a teacher's electronic stethoscope 12 and the electronic stethoscopes 12 of one or more students may be networked via the network interface 152. The physician or a student may be selected to sense the patient's body sounds, while the other networked users listen to the patient's body sounds via their respective electronic stethoscopes 12. In addition, sounds stored in the teacher's electronic stethoscope 12 (or in another networked storage device) may be played back at substantially the same time to all networked electronic stethoscopes 12. The physician may also provide voice instructions or prompts via the sensor 38 or microphone 48 on the main housing 36 that are provided through the ear pieces of the students' electronic stethoscopes 12 at the same time as the sensed body sounds. Thus, if the physician's electronic stethoscope is being used to sense body sounds, the physician can demonstrate positioning and use of the electronic stethoscope 12a while the students listen on networked electronic stethoscopes 12b-12n. If a student's electronic stethoscope is being used to sense body sounds, the physician can provide instruction and guidance to the each of the students via the sensor 38 or microphone 48. In addition, each of the students with an electronic stethoscope 12 networked to the network interface 152 can take a turn sensing the body sounds while the physician provides individual guidance to them.

In other embodiments, networked scopes are connected to a computer or other external device (e.g., cell phone, PDA) as described above. The auscultation sounds and voice signals of a networked scope may be reproduced in substantial real-time by speakers connected to the computer or other external device. In some embodiments, body sounds may be downloaded from an electronic storage medium or other online database (e.g., website) to the computer or external device via a network connection and streamed to the networked stethoscopes and/or reproduced in substantial real time by speakers.

In summary, certain embodiments disclosed herein relate to a telemedicine system including a first electronic stethoscope including a housing configured for hand-held manipulation by a clinician relative to a patient, a transducer supported by the housing and configured to sense auscultation signals from the patient at a first location, and a headset coupled to the housing and configured to deliver audio corresponding to the auscultation signals through earpieces on the headset. The telemedicine system further includes a second electronic stethoscope including a housing, transducer, and headset substantially similar to the housing, transducer, and headset of the first electronic stethoscope. The first electronic stethoscope is configured to convert the auscultation signals to digital signals representative of the auscultation signals and to wirelessly transmit the digital signals to a second location via a secure digital network. The second electronic stethoscope is configured to receive the digital signals representative of the auscultation signals at the second location via the secure digital network, to convert the digital signals to audio corresponding to the auscultation signals, and to deliver the audio through earpieces on the headset of the second electronic stethoscope in substantial real time with the sensing of the auscultation sounds at the first location.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

The invention claimed is:

1. A telemedicine system comprising:
a first electronic stethoscope comprising a housing configured for hand-held manipulation, a transducer that senses auscultation signals at a first location, and a headset that delivers audio corresponding to the auscultation signals through earpieces on the headset, the first electronic stethoscope further comprising a processor that converts the auscultation signals to digital signals representative of the auscultation signals and an antenna to wirelessly transmit the digital signals to a second location via a secure digital network; and
a second electronic stethoscope comprising a housing configured for hand-held manipulation, a transducer, and a headset that delivers audio through earpieces on the headset, the second electronic stethoscope further comprising an antenna to receive the digital signals representative of the auscultation signals at the second location via the secure digital network, and a processor to convert the digital signals to audio corresponding to the auscultation signals and deliver the audio through earpieces on the headset of the second electronic stethoscope in substantial real time with the sensing of the auscultation sounds at the first location,
wherein the transducer on the first electronic stethoscope further receives ambient audio at the first location and the transducer on the second electronic stethoscope further receives ambient audio at the second location, and wherein the ambient audio is transmitted wirelessly between the first and second locations via the secure digital network.

2. A telemedicine system comprising:
a first electronic stethoscope comprising a housing configured for hand-held manipulation, a transducer that senses auscultation signals at a first location, and a headset that delivers audio corresponding to the auscultation signals through earpieces on the headset, the first electronic stethoscope further comprising a processor that converts the auscultation signals to digital signals representative of the auscultation signals and an antenna to wirelessly transmit the digital signals to a second location via a secure digital network; and a second electronic stethoscope comprising a housing configured for hand-held manipulation, a transducer, and a headset that delivers audio through earpieces on the headset, the second electronic stethoscope further comprising an antenna to receive the digital signals representative of the auscultation signals at the second location via the secure digital network, and a processor to convert the digital signals to audio corresponding to the auscultation signals and deliver the audio through earpieces on the headset of the second electronic stethoscope in substantial real time with the sensing of the auscultation sounds at the first location, wherein the first electronic stethoscope is configured to receive control signals via the secure digital network to allow modification of settings of the first electronic stethoscope from the second location.

3. The telemedicine system of claim 1 or 2, wherein the audio delivered to the headset of the second electronic stethoscope is a faithful reproduction of the auscultation sounds at the first location.

4. The telemedicine system of claim 1, wherein the transducer is activated to receive ambient audio at the first location upon actuation of a user interface element on the first electronic stethoscope, and wherein the second transducer is activated to receive ambient audio at the second location upon actuation of a user interface element on the second electronic stethoscope.

5. The telemedicine system of claim 4, wherein the processor of the first electronic stethoscope comprises a frequency filter, and wherein actuation of the user interface element of the first electronic stethoscope modifies a setting of the frequency filter.

6. The telemedicine system of claim 1 or 2, wherein the first electronic stethoscope communicates with a first computer at the first location via a first secure personal area network and the second electronic stethoscope communicates with a second computer at the second location via a second secure personal area network, and wherein the first computer transmits the digital signals representative of the auscultation signals to the second computer via a secure digital connection.

7. The telemedicine system of claim 6, wherein at least one of the first stethoscope, second stethoscope, first computer, and the second computer provides an audio and/or visual indication when the audio delivered through the earpieces on the headset of the second electronic stethoscope is a faithful reproduction of the auscultation signals sensed by the first electronic stethoscope.

8. The telemedicine system of claim 1 or 2, wherein the antenna of each of the first and second electronic stethoscopes is disposed at least partially in the headset.

9. The telemedicine system of claim 1 or 2, wherein the first electronic stethoscope is further configured to wirelessly receive signals from the second electronic stethoscope via the secure digital network.

10. The telemedicine system of claim 1 or 2, wherein the second location is remote from the first location.

11. The telemedicine system of claim 2, wherein the control signals prevent modification of certain settings of the first electronic stethoscope at the first location.

12. The telemedicine system of claim 11, wherein the control signals do not prevent modification of volume settings of the first electronic stethoscope at the first location.

13. The telemedicine system of claim 1 or 2, wherein at least one of the first and second electronic stethoscopes comprises a wireless chestpiece and a wireless headset.

* * * * *